(12) United States Patent
Zalevsky et al.

(10) Patent No.: US 12,171,692 B2
(45) Date of Patent: Dec. 24, 2024

(54) SYSTEM, METHOD AND MATERIAL COMPOSITION FOR USE IN CORRECTION OF EYE CONDITIONS (71) Applicant: BAR ILAN UNIVERSITY, Ramat Gan (IL)

(72) Inventors: Zeev Zalevsky, Rosh HaAyin (IL); Jean Paul Lellouche, Ashdod (IL); David Smadja, Tel Aviv (IL); Yifat Harel, Holon (IL); Rivka Ben Ishay, Yakir (IL)

(73) Assignee: BAR ILAN UNIVERSITY, Ramat Gan (IL)

( * ) Notice: Subject to any disclaimer, the term of this patent is extended or adjusted under 35 U.S.C. 154(b) by 612 days.

(21) Appl. No.: 16/975,479

(22) PCT Filed: Feb. 27, 2019

(86) PCT No.: PCT/IL2019/050219
§ 371 (c)(1),
(2) Date: Aug. 25, 2020

(87) PCT Pub. No.: WO2019/167040
PCT Pub. Date: Sep. 6, 2019

(65) Prior Publication Data
US 2021/0022922 A1 Jan. 28, 2021

Related U.S. Application Data (60) Provisional application No. 62/636,936, filed on Mar. 1, 2018.

(51) Int. Cl.
*A61B 3/02* (2006.01)
*A61B 3/00* (2006.01)
(Continued)

(52) U.S. Cl.
CPC ...... *A61F 9/00825* (2013.01); *A61F 9/00745* (2013.01); *A61K 9/5169* (2013.01);
(Continued)

(58) Field of Classification Search
CPC ......... A61B 3/02; A61B 3/102; A61B 3/1025; A61B 3/1015; A61B 3/113; A61B 3/1225; A61B 3/024; A61B 3/005
(Continued)

(56) References Cited

U.S. PATENT DOCUMENTS 5,807,380 A * 9/1998 Dishler ............... A61F 9/00802
606/4
6,342,053 B1 * 1/2002 Berry ...................... A61F 9/008
606/5
(Continued)

FOREIGN PATENT DOCUMENTS

| CN | 106604695 A | 4/2017 |
|---|---|---|
| JP | 2002517085 A | 6/2002 |

(Continued)

OTHER PUBLICATIONS

Hai et al. ("Maghemite nanoparticles coated with human serum albumin: combining targeting by the iron-acquisition pathway and potential in photothermal therapies", The Royal Society of Chemistry, 2017, pp. 3154-3162). (Year: 2017).*
(Continued)

Primary Examiner — Dawayne Pinkney
(74) Attorney, Agent, or Firm — Dorsey & Whitney LLP (57) ABSTRACT A system, technique and material composition for use in correction of eye condition are disclosed. The system comprising a processing utility and an etching utility. The processing utility comprises: correction pattern module configured for providing a selected two-dimensional pattern in according with input data indicative of vision impermanent
(Continued)

of a user, and for generating operational instructions for forming said selected two-dimensional pattern on the surface of the cornea by said etching utility. The etching utility is configured to etching the selected patter on surface of the cornea of a user. The material composition comprises aqueous solution comprising a plurality of nanoparticles, said nanoparticles comprising maghemite nanoparticles wrapped by biocompatible protein chains. The material composition may be used as eye drops thereby allowing the nanoparticles to occupy etched region on the cornea, thereby maintaining correction of eye condition.

19 Claims, 12 Drawing Sheets

(51) Int. Cl.
  *A61B 3/10* (2006.01)
  *A61F 9/007* (2006.01)
  *A61F 9/008* (2006.01)
  *A61K 9/51* (2006.01)
  *A61K 9/00* (2006.01)
  *B82Y 5/00* (2011.01)

(52) U.S. Cl.
  CPC ............ *A61F 2009/00872* (2013.01); *A61F 2009/00885* (2013.01); *A61F 2009/00897* (2013.01); *A61K 9/0048* (2013.01); *B82Y 5/00* (2013.01)

(58) Field of Classification Search
  USPC ........ 351/200, 205–206, 209–210, 221–223, 351/245–246
  See application file for complete search history.

(56) References Cited

U.S. PATENT DOCUMENTS

| | | | |
|---|---|---|---|
| 7,859,769 B2 | 12/2010 | Zalevsky | |
| 2002/0055736 A1* | 5/2002 | Horn | A61F 9/013 606/26 |
| 2006/0287662 A1* | 12/2006 | Berry | A61F 9/0079 606/166 |
| 2008/0027418 A1 | 1/2008 | Berry | |

FOREIGN PATENT DOCUMENTS

| | | |
|---|---|---|
| JP | 2003532484 A | 11/2003 |
| WO | 0185045 A1 | 11/2001 |

OTHER PUBLICATIONS

"Israeli Ophthalmologists Invents Revolutionary Eyedrops that could Replace Eyeglasses", http://webcache.googleusercontent.com/search?q=cache:X-LJHPmRpNgJ:https://interestingengineering.com/israeli-ophthalmologists-invents-revo, 2018, 2.

Ah et al., "Aggregation Control of Hydrophilic Maghemite (Gamma-Fe2O3) Nanoparticles by Surface Doping Using Cerium Atoms", Institute for Nanotechnology and Advanced Materials, Bar Ilan University, Abstract Only, 2010, 1.

Hai et al., "Maghemite Nanoparticles Coated with Human Serum Albumin: Combining Targeting by the Iron-Acquisition Pathway and Potential in Photothermal Therapies", The Royal Society of Chemistry, 2017, pp. 3-11.

Kompella et al., "Nanomedicines for Back of the Eye Drug Delivery, Gene Delivery, and Imaging", University of Colorado Anschutz Medical Campus, 2013, pp. 1-54.

Levy et al., "Bioactive Magnetic Near Infra-Red Fluorescent Core-Shell Iron Oxide/Human Serum Albumin Nanoparticles for Controlled Release of Growth Factors for Augmentation of Human Mesenchymal Stem Cell Growth and Differentiation", Journal of Nanobiotechnology, 2015, pp. 1-14.

Raju et al., "Nanotechnology for Ocular Therapeutics and Tissue Repair", University of Miami Miller School of Medicine, 2008, pp. 431-436.

Siegel, "New Eyedrops Could Repair Corneas, Make Glasses Unneccessary", The Jerusalem Post, 2018, 2.

PCT, "International Search Report," Application No. PCT/IL2019/050219, mailed Jun. 2, 2019, 2 pages.

* cited by examiner

Encapsulated Nanoparticules identified inside a corneal incision as tiny hyperefective balls of 60-80 nm diameter

SYSTEM, METHOD AND MATERIAL COMPOSITION FOR USE IN CORRECTION OF EYE CONDITIONS

TECHNOLOGICAL FIELD

The present invention is in the field of visual correction techniques and specifically relates to correction of visual impediments such as myopia, hyperopia, presbyopia, astigmatism and other visual impediments.

BACKGROUND

Various eye conditions are known as limiting vision. Such eye conditions may generally include nearsightedness (myopia), farsightedness (hyperopia), and aging of the eye (typically associated with (presbyopia). Various techniques are known providing correction to such eye conditions, including glasses, contact lenses as well as intra-ocular lenses. The lenses used are provided with selected one or more optical powers and/or selected patterns designed for increase of depth of focus of the lens in accordance with user's eye condition. One of the commonly used approaches to overcome various eye conditions, e.g. presbyopia symptoms, is based on advanced intra ocular lenses technology, through either accommodating IOLs, multifocal IOLs or more recently, IOLs with extended depth of focus.

Optical power may generally be provided using refractive manipulation of light path. However, diffractive techniques for manipulation of optical path may also provide suitable optical power. Such techniques may include Fresnel zone plates, or rings, providing diffraction of light in a lens-like fashion. Additional light manipulation techniques may utilize light interference for extension of depth of focus.

For example, U.S. Pat. No. 7,859,769 provides an imaging arrangement and method for extended the depth of focus. The imaging arrangement comprises an imaging lens having a certain affective aperture, and an optical element associated with said imaging lens. The optical element is configured as a phase-affecting, non-diffractive optical element defining a spatially low frequency phase transition. The optical element and the imaging lens define a predetermined pattern formed by spaced-apart substantially optically transparent features of different optical properties. Position of at least one phase transition region of the optical element within the imaging lens plane is determined by at least a dimension of said affective aperture.

Protein based drug delivery systems enable encapsulation of selected drugs and provide stable, non-toxic and typically non-antigenic carriers. Human serum albumin is of interest as drug carrier compound being highly abundant plasma protein and has long half-life.

GENERAL DESCRIPTION

The present invention provides a novel technique for correction of eye conditions causing visual difficulties to users. The present technique provides for applying pattern, selected in accordance with user's eye condition, on the cornea of the user, and introducing selected material composition providing refractive index variation onto the applied pattern. Generally, the selected material composition is in the form of eye drops comprising synthetic nanoparticles providing local modification of the refractive index of the cornea through an enhanced optical pattern stamped onto the superficial epithelial layers of the cornea. This optical pattern would provide a temporary and targeted correction of the refractive errors without modifying the corneal shape.

The selected material composition may generally be provided in the form of eye drops comprising maghemite nanoparticles, typically carried by albumin shell, e.g. human serum albumin (HAS). The material composition is selected as biocompatible non-toxic material composition having high stability both on shelf and on the user's cornea. The maghemite-albumin nanoparticles being characterized by high refractive index, which, when incarcerated into the corneal epithelium through the patterned applied thereon, provide for modifying refractive index and total eye refraction in accordance with the selected pattern.

Further, the present invention provides for a system for use in correction of eye condition associated with visual conditions, e.g. such as myopia, hyperopia or presbyopia. The system comprising a processing utility and an etching utility and configured for receiving input data indicative of eye condition of the user. The processing utility is configured for being responsive to the input data and for determining two-dimensional pattern for correcting visual impediment in accordance with the input data. The processing utility may typically comprise a correction pattern module configured for determining mapping of the selected two-dimensional pattern in according with input data indicative of vision impermanent of a user. The processing utility is further configured for generating operational instructions for forming the selected two-dimensional pattern by said etching utility. The etching utility typically comprises at least one laser unit and beam steering module. The etching utility is configured for providing optical energy and for directing the optical energy in accordance with operational instructions for etching the selected pattern on cornea of user's eye.

Thus, according to a broad aspect, the present invention provides a system for use in correction of eye condition, the system comprising a processing utility and an etching utility; the processing utility comprises:
  correction pattern module configured for providing a selected two-dimensional pattern in according with input data indicative of vision impermanent of a user, and for generating operational instructions for forming said selected two-dimensional pattern on the surface of the cornea by said etching utility;
  the etching utility is configured to etching the selected patter on surface of the cornea of a user.

According to some embodiments, the etching utility is configured for transmitting selected ultra-sound waves for etching said pattern on the user's cornea.

According to some other embodiments, the etching utility is configured for mechanical etching of the cornea.

According to yet some other embodiments, the etching utility comprises at least one laser unit and beam steering module and is configured for providing optical energy for etching a selected pattern in accordance with operation instructions on cornea of user's eye.

The laser unit may be configured to provide etching at depth of up to single cell layer of the cornea.

According to some embodiments, the two-dimensional pattern comprises a diffractive pattern. For example, the pattern may comprise Fresnel rings pattern.

According to some embodiments, the two-dimensional pattern comprises or phase affecting interference pattern. The pattern may for example comprise an extension of depth of focus pattern.

According to some embodiments, the selected pattern enables optical correction at optical power resolution between 0.1 and 0.3 diopter. Generally, this allows corrections lower than 0.25 diopter, which is the general limit of convention optical correction.

According to one other broad aspect of the invention, the invention provides a material composition comprising solution comprising a plurality of nanoparticles, said nanoparticles comprising maghemite nanoparticles wrapped by biocompatible protein chains.

According to some embodiments, the protein chains comprise human serum albumin proteins The material composition may be configured for use in correction of visual impediment. The material composition may preferably be configured for use as eye drops.

According to some embodiments, the material composition may be configured for use as eye drops after applying etching of selected patterns to cornea of a user, said nanoparticles being dispersed within surface relief of the cornea to provide optical power addition to that of the user's eye.

According to some embodiments, the maghemite nanoparticles comprise Ceric Ammonium Nitrate Fe2O3 nanoparticles.

According to some embodiments, the maghemite nanoparticles wrapped by biocompatible protein chains are further configured for carrying one or more selected drugs.

According to yet another broad aspect of the invention, the invention provides a material composition for use in treatment of visual impediments, the material composition comprising nanoparticles comprising maghemite based particles within protein shell. The nanoparticles may further be configured as drug carrier and delivery.

The invention further contemplates a maghemite macrostructure, a formulation comprising same and methods for its preparation.

The formulation provided in accordance with the invention may be an ophthalmological formulation (for ocular use), e.g., in the form of eye drops, comprising a maghemite macrostructure, typically constituting a modified maghemite associated with a biocompatible macro-carrier such as a peptide, a polysaccharide and others. The modified maghemite comprises maghemite (iron oxide having the repeating units $\gamma$-$Fe_2O_3$) associated with ceric ammonium nitrate (CAN). The macrostructure is formed by encapsulating the modified maghemite nanoparticles within a matrix of the macro-carrier, thus forming the macrostructure.

In some embodiments, the macro-carrier is a peptide. In some embodiments, the macro-carrier is albumin, e.g. human serum albumin (HAS).

The macrostructure may be provided in a solid powder reconstitutable form or in an aqueous carrier as a liquid read-for-use ophthalmological formulation. The aqueous carrier may be any one of water, bacteriostatic water, sodium chloride solutions, glucose solutions, liquid surfactant, pH-buffered solution and others.

Where the macrostructure is provided in an aqueous medium, it may be treated to afford the reconstitutable powder form. The powder form may be obtained by lyophilization or spray drying techniques.

Also provided is a kit, optionally in the form or eye drops or a powder for reconstitution, that comprises a solid powder in a reconstitutable form or an aqueous formulation, and instructions of use. Where the kit comprises the powder, it may also include at least one aqueous carrier for reconstituting the macrostructure.

According to yet another broad aspect, the present invention provides a kit for use in correction of visual impediments, the kit comprises the system described above and the eye drops comprising material composition described above.

The kit may further comprise instruction manual for operating said system for etching a selected pattern on the user's cornea and applying the eye drops into the eye. Generally, the kit allows optical correction to user who cannot undergo LASIK surgery as the pattern etching is shallow on the cornea and may be done of thin cornea. Thus, the kit may be suitable for use at home or at a doctors' clinic. Further, the kit and technique enable correction to users who already had cataract surgery as well, enabling additional correction over intro ocular lenses already used by the user.

According to some embodiments, the material composition comprising maghemite nanoparticles wrapped by biocompatible protein chains being configured for increasing stability of optical effect of said pattern thereby enabling optical correction effect lasting between a few days and a few months.

According to some embodiments, the kit may be configured for correction of any one of myopia, hyperopia, presbyopia, and astigmatism.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 8A and 8B show FTIR spectroscopy of HAS core NPs carrying maghemite nanoparticles according to some embodiments of the invention, FIG. 8A shows FTIR results and FIG. 8B focuses on peaks in the absorption spectrum of the Maghemite carrying HSA nanoparticles;

DETAILED DESCRIPTION OF EMBODIMENTS

Figure 1:
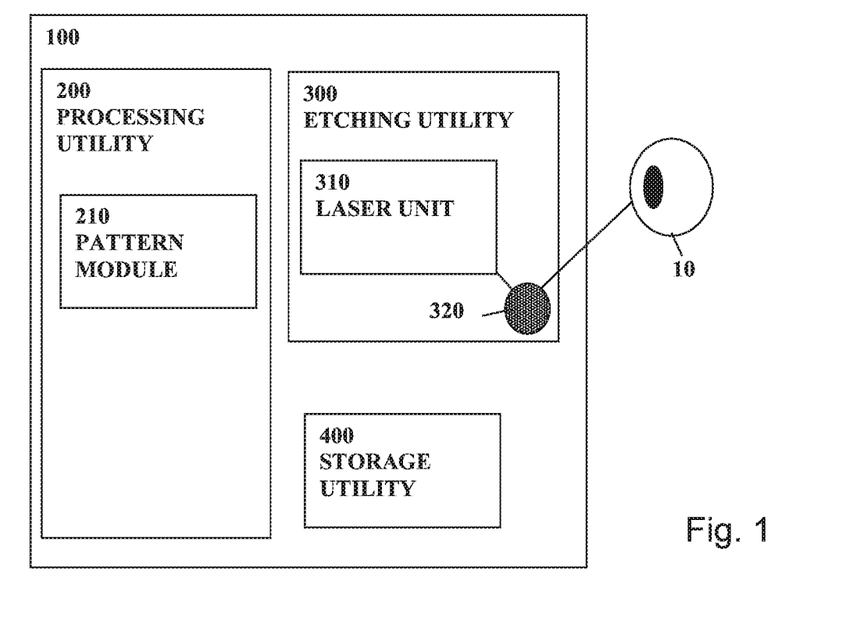
FIG. 1 schematically illustrates a system for use in correction of eye condition according to some embodiments of the invention.

As indicated above, the present technique provides for correction of visual impediments such as myopia, hyperopia and presbyopia. FIG. 1 shows a schematic illustration of system 100 for use in use in correction of eye condition. The system 100 includes a processing utility 200 and an etching utility 300. The system may generally be configured as a computer system, while being associated with the etching utility 300 to provide output pattern writing. To this end, the system 100 may also include storage utility 400 as well as input/output utility and user interface that are not specifically shown in FIG. 1.

The processing utility 200 may generally include one or more processors and further include one or more hardware or software modules such as correction pattern module 210. The correction pattern module 210 is configured for receiving and processing input data indicative of required optical correction for a user's eye (each eye may require different optical correction) and for determining, or retrieving from a storage utility, a selected two-dimensional pattern suitable for the optical correction. The processing utility 200 is further configured for generating operational instructions for etching the selected pattern on cornea of the user to provide the selected optical correction.

Figure 2:
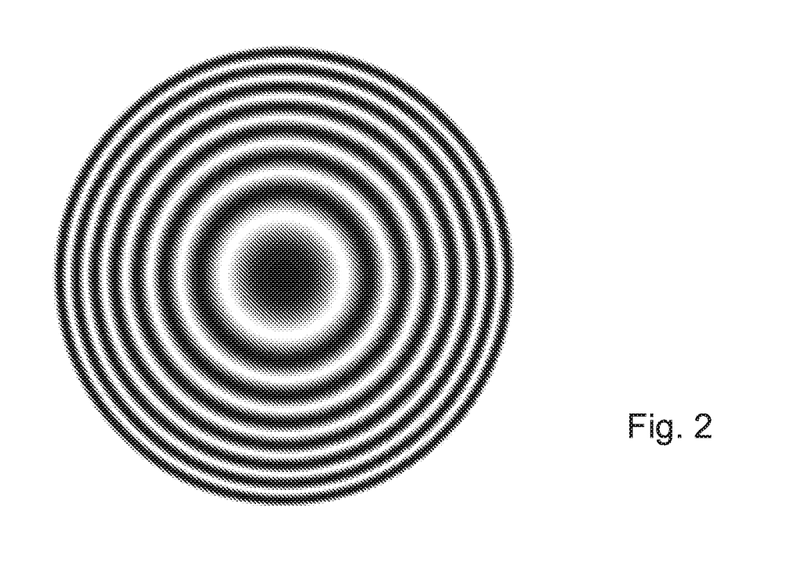
FIG. 2 exemplifies Fresnel zone plate pattern suitable for correction of eye condition by adding/subtracting optical power.
Figure 3:
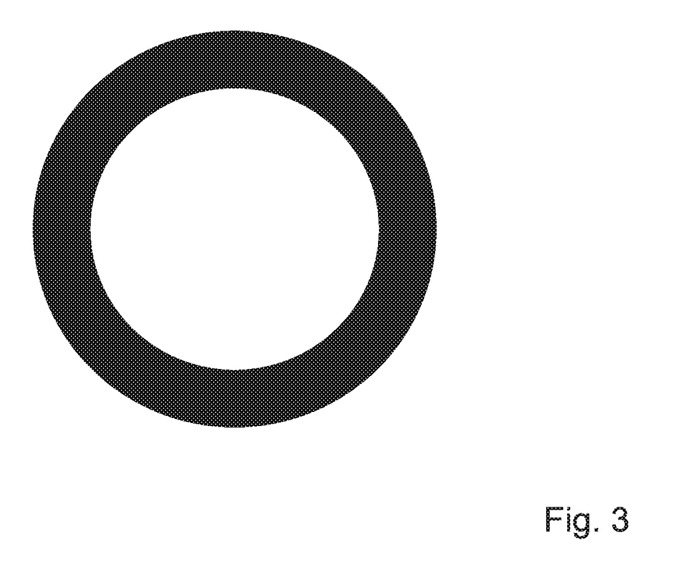
FIG. 3 and FIG. 4 exemplify eye correction patterns associated with extension of depth of focus of the eye's lens.
Figure 4:
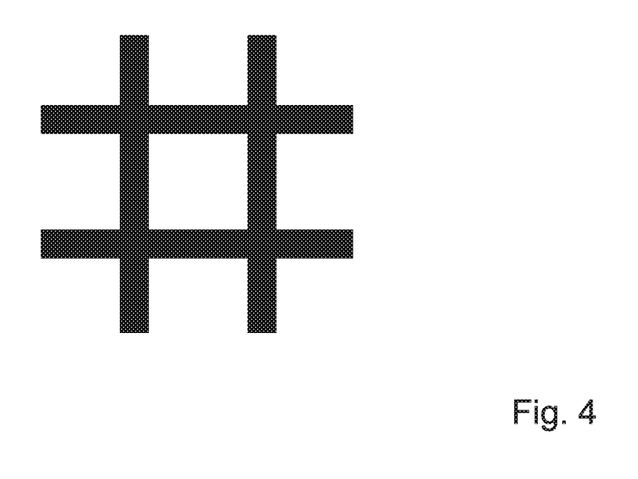

The processing utility 200 transmits the generated instructions to the etching utility 300 for providing optical radiation and directing it for generating the selected pattern on cornea of a user's eye. FIGS. 2, 3 and 4 exemplify schematically three possible patterns selected in accordance with eye condition of the user. FIG. 2 shows Fresnel zone plate pattern including a plurality of concentric rings of varying widths; FIGS. 3 and 4 exemplify patterns selected for extension of depth of focus, e.g. suitable for correction of presbyopia. Generally, the optical characteristics of such patterns and the exact configuration of each pattern can be determined in accordance with selected eye correction, e.g. optical power required for correction, or required increase of depth of focus.

Generally, the etching utility 300 is configured to apply the selected patterns as incision onto the epithelial layers of the cornea. The etching may generally be provided using optical etching with selected wavelength ranges, ultra-sonic etching and/or mechanical incision of the cornea. For simplicity the etching utility is exemplified herein as optical etching utility 300 configured with laser light source, and a beam steering unit 320. The laser light source 310 is configured to provide optical radiation at wavelength and power suitable for etching within epithelial cell later and the steering unit 320 is configured for varying path of the output light beam to enable projection of the selected pattern on the user's cornea. Operation speed of the steering unit 320 and power of the light source unit 310 are selected to provide light etching of the cornea, typically, within superficial epithelial layers, e.g. at depth of single cell layer.

More specifically, the pattern is generally to be etched onto user's cornea with depth of no more than one cell layer, or up to a few micrometers, to avoid any damage to the user's eye and allow the cornea to heal and renew the etched cell layer. It should also be noted that the selected optical pattern is effectively stamped onto the superficial epithelial layers of the cornea.

As indicated above, the pattern is selected to provide additional optical power, or vary depth of focus of the user's eye. To provide lasting effect, the present technique utilizes appropriate eye drop solution, including selected nanoparticles having refractive index different than that of the cornea and/or tears around the eye. To this end, the eye drop formulation generally includes maghemite particles carried by albumin shell. More specifically, the albumin shell is typically in the meaning of protein folding around the maghemite particles. The nanoparticles may be based on Ceric Ammonium Nitrate (CAN) modified Maghemite ($\gamma$-$Fe_2O_3$) particles.

It should be noted that the particles of the eye solution are configured to provide optical effect of the inscribed pattern to be steady in time. More specifically, the nanoparticles generally enter the incision/etching region thus presenting tears from arriving to the location. This enables to maintain the optical effect and limits healing process of the epithelial layers to provide the optical effect to last from a few days to a few months. Generally, in regular conditions without the use of the nanoparticles' eye drops, the etching pattern may be healed within 1-2 days.

Generally, protein-based NPs, often used as drug carrier particles, may be of high interest for the eye drop solution, based on high stability during storage, and biocompatibility, e.g. being non-toxic and non-antigenic. Albumin proteins provide macromolecular carrier that has been shown to be biodegradable, non-immunogenic, non-toxic, and metabolized in vivo.

In some embodiments of the invention the nanoparticles may include Human Serum Albumin (HSA, 66.5 kDa). HAS may be preferred since it is the most abundant plasma protein (35-50 g/L human serum) and has an average half-life of 19 days, and is thus used in the following, however it should be noted that the nanoparticles of the present invention may typically be associated with any albumin type protein including various animal serum and/or synthetic albumin. Generally, albumin contains 35 cysteinyl residues forming one sulfhydryl group and 17 disulfide bridges. HSA is robust towards pH, it is stable in the pH range of 4-9. Further, HSA can be heated at 60° C. for up to 10 h.

Figure 5:
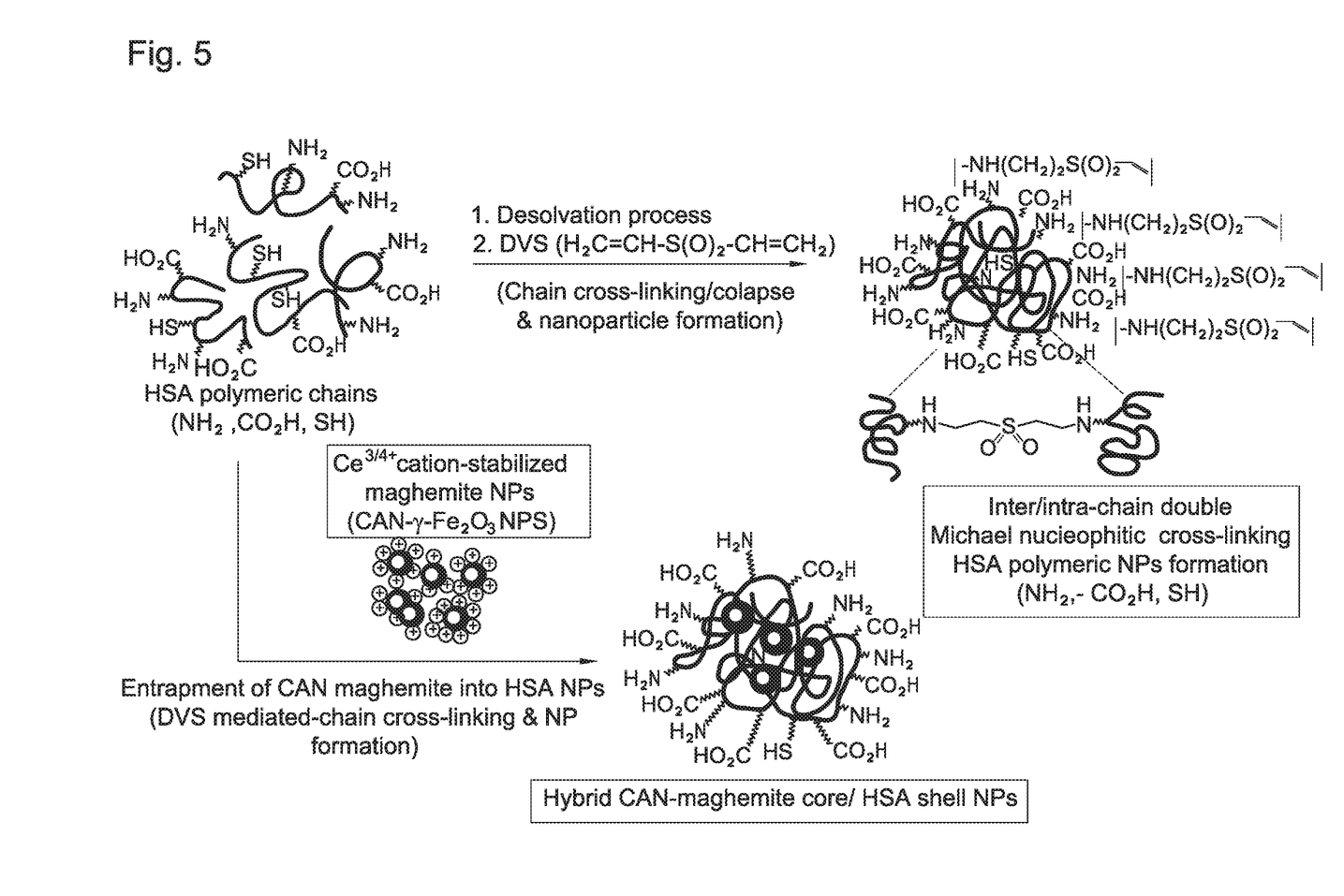
FIG. 5 exemplifies desolvation process of albumin proteins according to some embodiments of the invention.
Figure 6A:
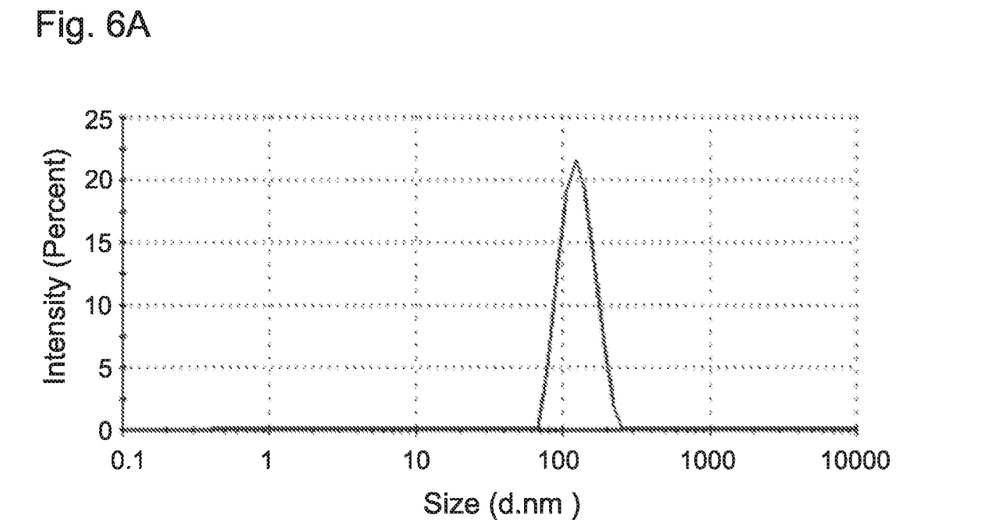
FIGS. 6A and 6B show size and electric (zeta) potential measurement of nanoparticle produced according to some embodiments of the invention.
Figure 6B:
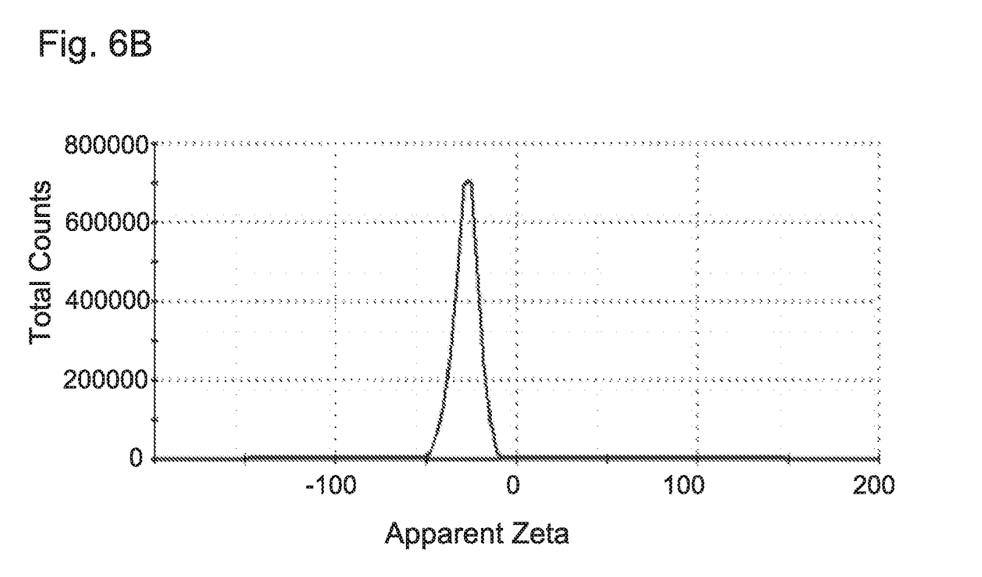
Figure 7A:
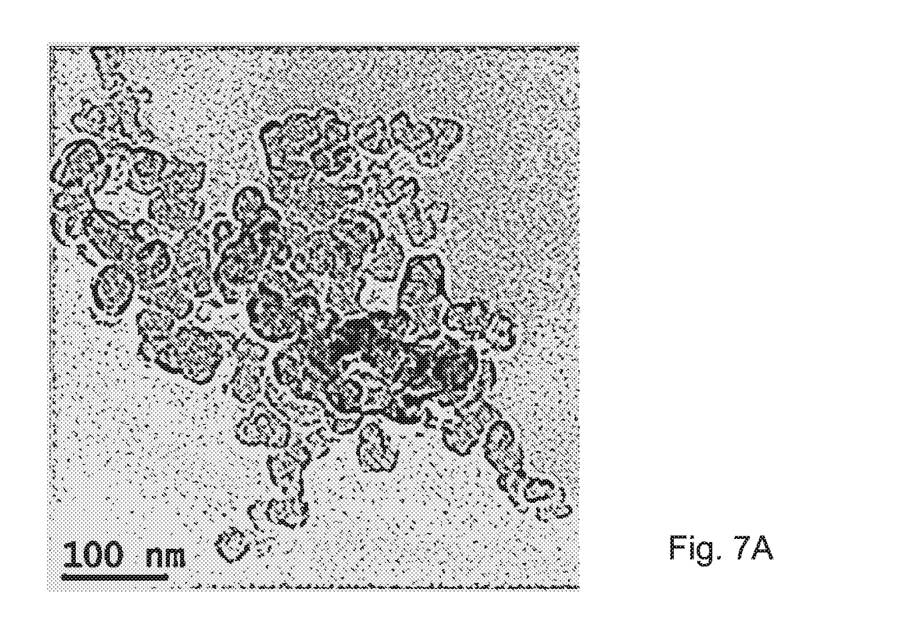
FIGS. 7A to 7C show TEM, cryo-TEM microphotographs and size distribution histogram of the HAS core NPs.
Figure 7B:
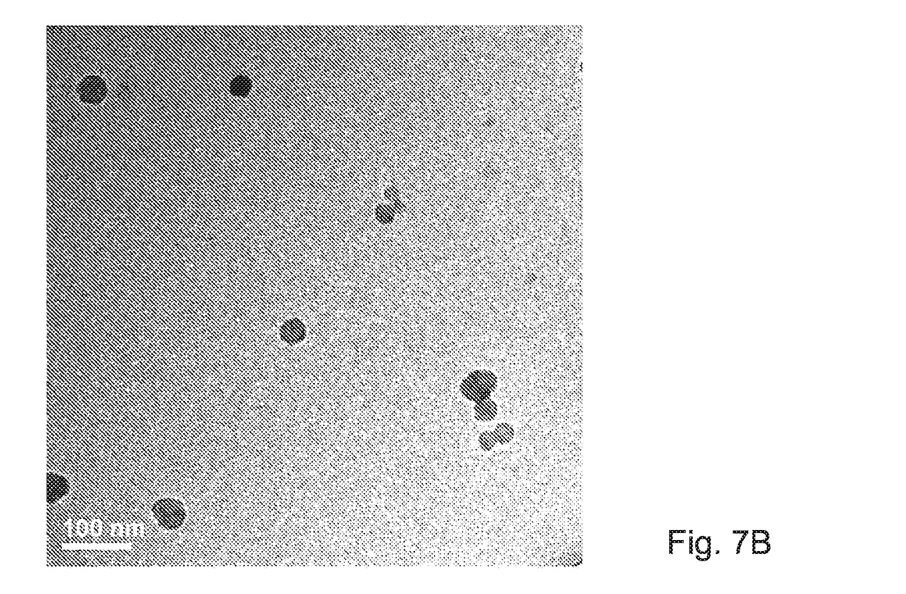
Figure 7C:
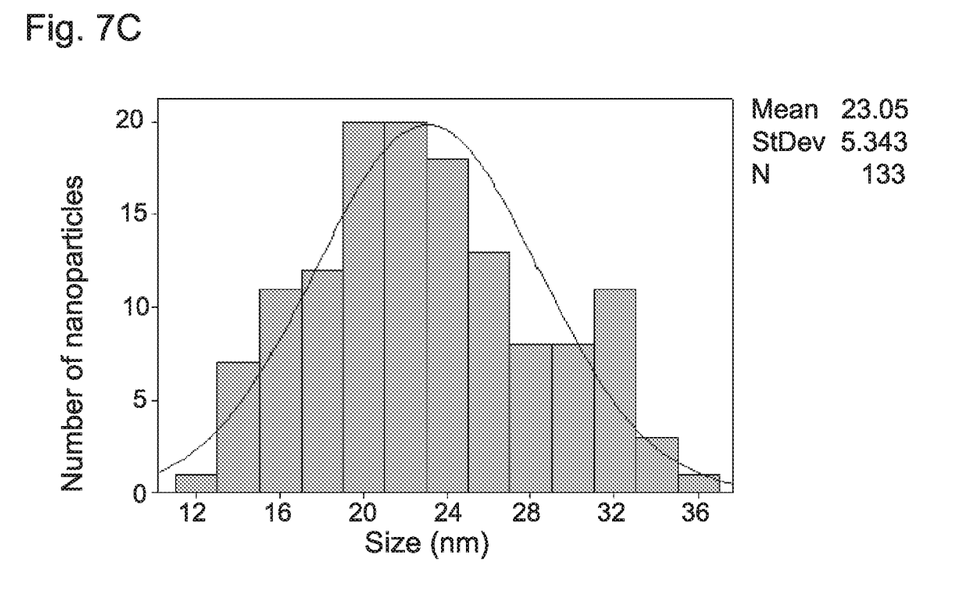
Figure 8A:
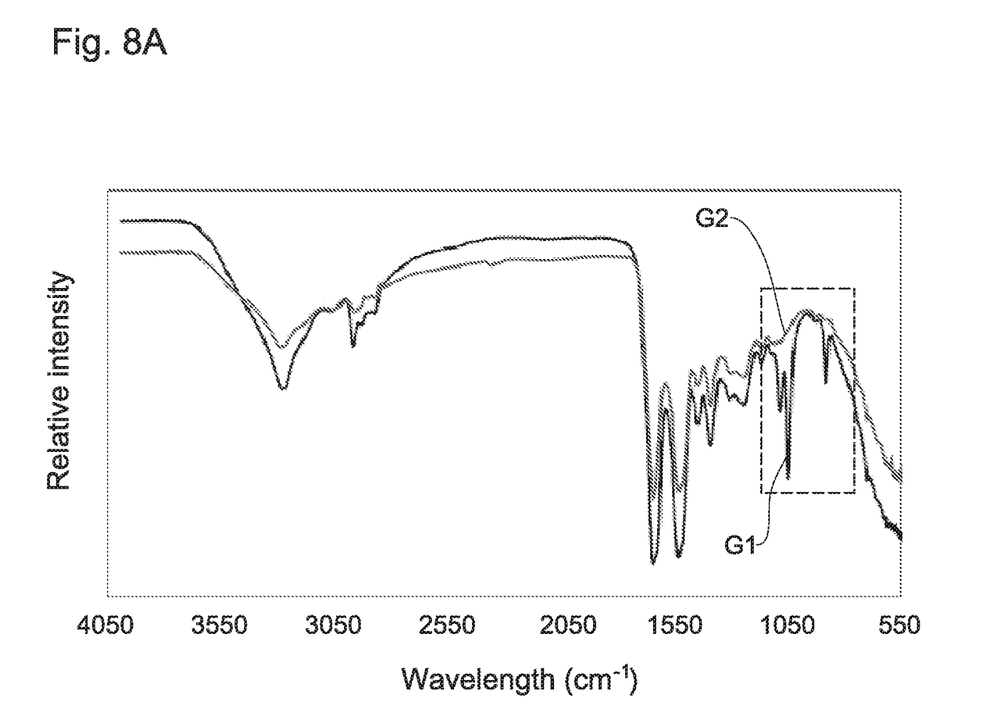
Figure 8B:
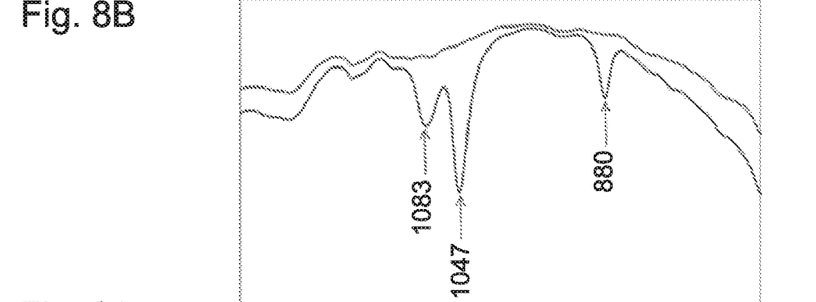
Figure 9A:
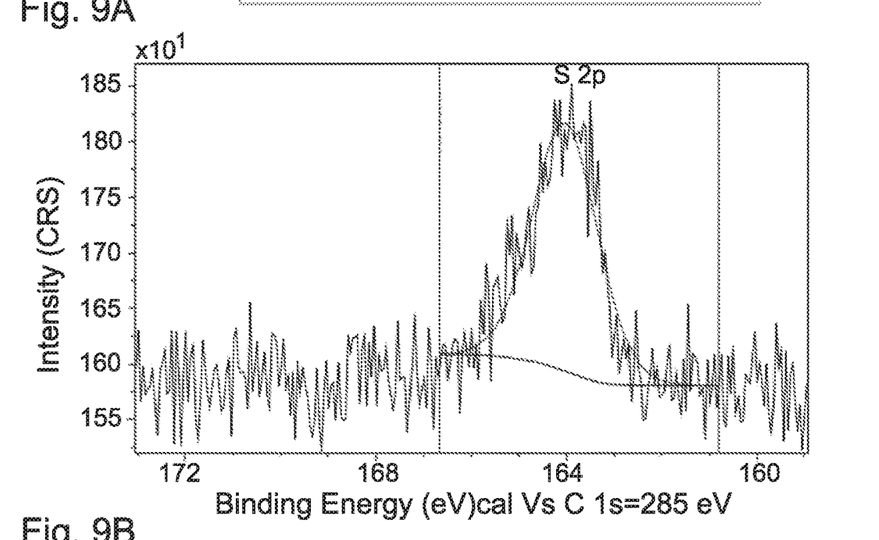
FIGS. 9A and 9B show X-ray photoelectron (XPS) spectra of the crude HAS (FIG. 9A) and HAS NPs described herein (FIG. 9B)
Figure 9B:
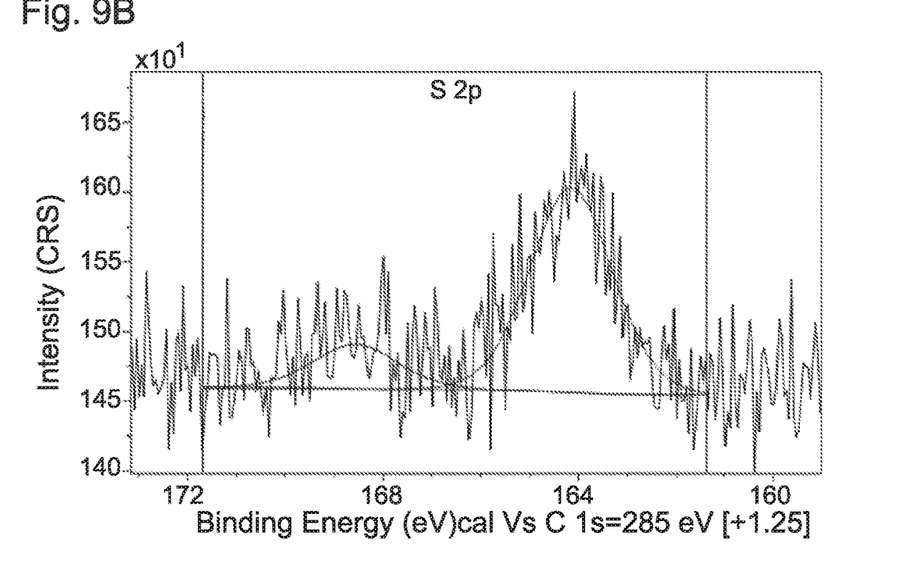

The inventors of the present invention have identified a technique enabling to provide and characterize HSA-based nanoparticles (NPs) having robust and controllable particle size. The technique utilizes desolvation/cross-linking-type Divinyl Sulfone (DVS)-mediated nanofabrication method exemplified in FIG. 5. During the desolvation process, coacervates are formed and then hardened/stabilized by cross-linking promoted by DVS. In this context, an HSA-based polymeric intra- and inter-chain collapse may originate from a controlled bidirectional covalent Michael reaction that may exploit the strong electrophilic properties of the bifunctional Divinyl Sulfone (DVS) reagent. The use of Divinyl Sulfone (DVS) as a cross-linker for the preparation of such HSA NPs, may offer the availability of a variety of free functional groups on their surface that may be used for further second step functional modifications. Moreover, related hybrid organic/inorganic nanosystems consisting of HSA NPs that encapsulated hydrophilic $(NH_4)_2Ce(IV)(NO_3)_6$ (Ceric Ammonium Nitrate-CAN) modified $\gamma$-$Fe_2O_3$ NPs (CAN-maghemite or CAN-$\gamma$-$Fe_2O_3$) NPs have also been fabricated and characterized. Several suitable nanoparticles have been produced and characterized, being nanoparticles variations/species and/or nanoparticles associated with intermediate production stages according to the present technique, as exemplified in the following.

Example 1—HSA Core Nanoparticles Fabrication

HSA Core Nanoparticles Fabrication HSA (50.0 mg) was dissolved in 1.0 mL of purified water (dd$H_2O$). Ethanol was 
added during the desolation process to get a total volume of 5.0 mL for a final HSA concentration of 10 mg/ml. 140.0 µL of DVS (5% w/w in EtOH) was added to induce protein chain cross-linking. The cross-linking process was performed by stirring the suspension for 1 hour at 55° C. followed by 20 minutes in an ultra-sonication bath. The resulting HSA nanoparticles were then purified by three cycles of differential centrifugation (at conditions of 13,500 rpm, 60 min, 4° C.) and were then re-dispersed to the original volume of $ddH_2O$. Each redispersion step was performed in an ultra-sonication bath for 10-15 min. To enable long-term storage and to avoid agglomeration, the nanoparticles were stored in a refrigerator at 4° C.

Example 2—CAN Maghemite Nanoparticle Preparation

The CAN Maghemite NP ($(CeL_n)^{3/4+}$-γ-$Fe_2O_3$) preparation was executed in a two-step procedure which included basic co-precipitation of two types of $Fe^{2+/3+}$ salts. This procedure yielded magnetite ($Fe_3O_4$) NPs as the less oxidized starting NP material that was then oxidized by monoelectronic oxidant cerium ammonium nitrate (CAN) and surface modified by $(CeL_n)^{3/4+}$ cation/complex NP surface doping, to obtain 6.61±2.04 nm-sized positively charged (+45.7 mY) CAN-γ-$Fe_2O_3$ NPs.

Example 3—Hybrid CAN Maghemite-Containing HSA Nanoparticles Preparation

To provide the desired nanoparticle structures, having suitable refractive index for affecting vision in accordance with selected pattern on the cornea, both of the nanoscale components of HSA and CAN-γ-$Fe_2O_3$ NPs were assembled for CAN-γ-$Fe_2O_3$ NPs to be entrapped into HSA nanocomposite particles during this same DVS-mediated NP fabrication/component cross-linking. For this purpose, the hybrid CAN maghemite containing HSA nanoparticles were prepared by procedure identical to the one described above for HSA NPs. In brief, to HSA (50.0 mg in 1.0 mL of $ddH_2O$), CAN-γ-$Fe_2O_3$ NPs were added at weight ratio of 25:1, and incubated for 1 hour at room temperature followed by a desolvation and cross-linking process. The resulting composite nanoparticles were then purified by three cycles of differential centrifugation (13,500 rpm, 60 min, 4° C.), magnetically decanted (using a strong external magnet) and re-dispersed into the original volume of $ddH_2O$. At each performed re-dispersion step, the reaction vessel was placed in a low power ultra-sonication bath for 15 min before processing. For a long-term storage and to avoid agglomeration, the nanoparticles were stored in a refrigerator (4° C.).

The resulting HSA core NPs were further characterized by various combined analytical, spectroscopic, and microscopic methods. FIGS. 6A and 6B show analysis of size distribution (FIG. 6A) and charge distribution (zeta potential, FIG. 6B) of the nanoparticles. The resulting fabricated HSA NPs show NP hydrodynamic size (OLS) of 149.56±1.8 nm and a strong negative zeta (electric) potential of −35.4±2.4 mV. Additionally, the nanoparticles show small dispersity, associated with polydispersity index (PDI) value of 0.17.

FIGS. 7A to 7C show TEM, cryo-TEM microphotographs and size distribution histogram of the HAS core NPs. These measurements indicate formation of spherical and substantially homogeneous HSA core NPs with an average size of 23.05±5.3 nm.

Additional measurement of the nanoparticles has been performed for determining cross-linking of the HSA polymeric chains by the DVS reagent. FIGS. 8A and 8B show FTIR spectrum measurement showing structural differences between standard HAS G2 and Maghemite carrying HSA nanoparticles G1 as described herein. FIG. 8A shows relative intensity measured along the spectrum between 4050 $cm^{-1}$ and 550 $cm^{-1}$, FIG. 8B focuses on a region marked by rectangle in FIG. 8A and specifically shows peaks in the absorption spectrum G1. The structural differences between the particles are exemplified by the FTIR absorption peaks variations are generally assigned to the presence of DVS in the core HSA NPs. The spectral difference between both the crude HSA and the HSA NP spectra can readily be seen in FIG. 8B at the range of 800-1100 $cm^{-1}$. The figure shows several peaks in the HSA NP spectrum G1 that do not appear in the standard HSA FTiR spectrum G2. The first peak at 880 $cm^{-1}$ corresponds to the stretching vibrations of the C—S bonds. The two other peaks appearing at 1047 and 1083 $cm^{-1}$ can be attributed to the stretching vibrations of the sulfoxide groups (R—S═O).

Additionally, X-ray photoelectron (XPS) spectroscopy was used to confirm the participation of this electrophilic DVS reagent during the HSA polymeric chain cross-linking FIGS. 9A and 9B show XPS spectra of the crude HAS (FIG. 9A) and HAS NPs described herein (FIG. 9B). The XPS analysis of HSA NPs shows that the S element is present in two oxidation states, i.e., a first state corresponding to the R—S species (Binding Energy of BE=164.0 eV) and the second state is at a higher binding energy, typically of 168.5 eV, corresponding to the $SO_2$ sulfoxide groups originating from the DVS sulfone group. This peak at 168.5 eV did not appear in the XPS analysis of the starting crude HSA protein.

The main functional groups, generally including the primary amine ($NH_2$) and the carboxylic groups (COOH), have been successfully quantified using a UV-sensitive Kaiser Test (1,3-diaminopropane use for EDC-activated COOH group amidation/derivatization). Both the obtained differential EDC and the non-EDC-based Kaiser results revealed that for 1.0 g of HSA NPs, there are 0.632 and 1.127 millimole of both the $NH_2$ and the COOH groups, respectively. (These quantified surface functionalities enable the future uses of HSA NPs as a biocompatible biodegradable drug carrier, as it allows further binding of additional therapy and/or tumor and diseased cell targeting agents).

Example 4—Hybrid HSA Entrapped-CAN-Maghemite NPs (CAN-γ-$Fe_2O_3$) Nanocomposite Particles Both nanoscale components HSA and positively charged CAN-γ-$Fe_2O_3$ having size of 6.61±2.04 nm and electric potential of +45.7 mV) were assembled by entrapment of the CAN-γ-$Fe_2O_3$ nanoparticles into the HSA NPs during the DVS-mediated NP fabrication step. For this purpose, hydrophilic water-compatible CAN-γ-$Fe_2O_3$ NPs have been used. Hybrid HSA/CAN-γ-$Fe_2O_3$ NPs were synthesized based upon the same DVS-mediated process as mentioned above. The weight ratio between both HSA and CAN-γ-$Fe_2O_3$ NPs phases were has been found to be 25:1 for an optimal encapsulation of a maghemite composition into a HSA nano shell. Generally, the weight ratio may be in the range between 15:1 and 40:1.

Thus, the DLS hydrodynamic diameter, the size distribution, and the electric potential values of the corresponding composite particles, have been determined. A DLS hydrodynamic diameter of 130 nm was measured with a polydispersity index below 0.3. An electric potential analysis was also performed in order to check the colloidal stability of the resulting hybrid NPs (the entrapment method) towards an aggregation control, meaning that composite particles were always found to be negatively charged with an average electric potential value of −25 mV.

Figure 10A:
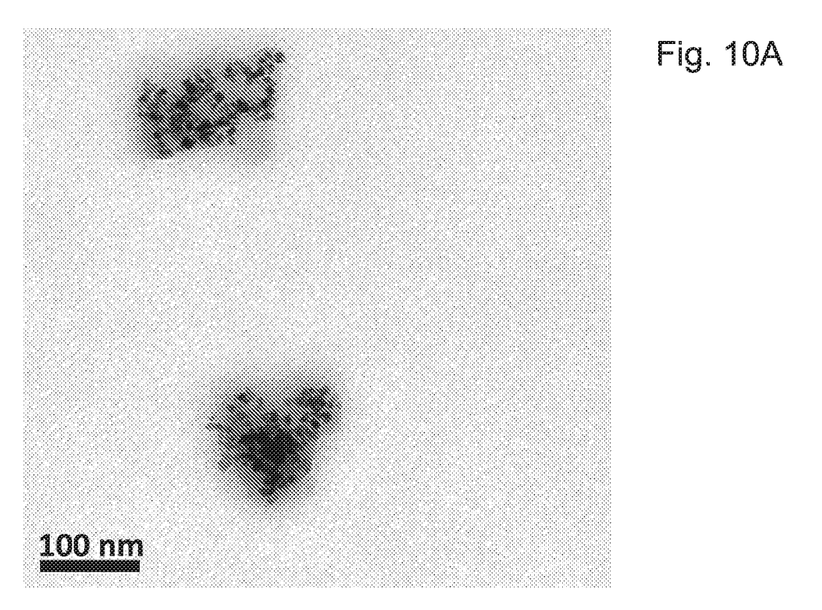
FIG. 10A to 10D show morphology and the size distribution measurements of the hybrid HSA/CAN-$\gamma$-$Fe_2O_3$ nanoparticles were characterized using TEM, cryo-TEM, and HR-SEM.
Figure 10B:
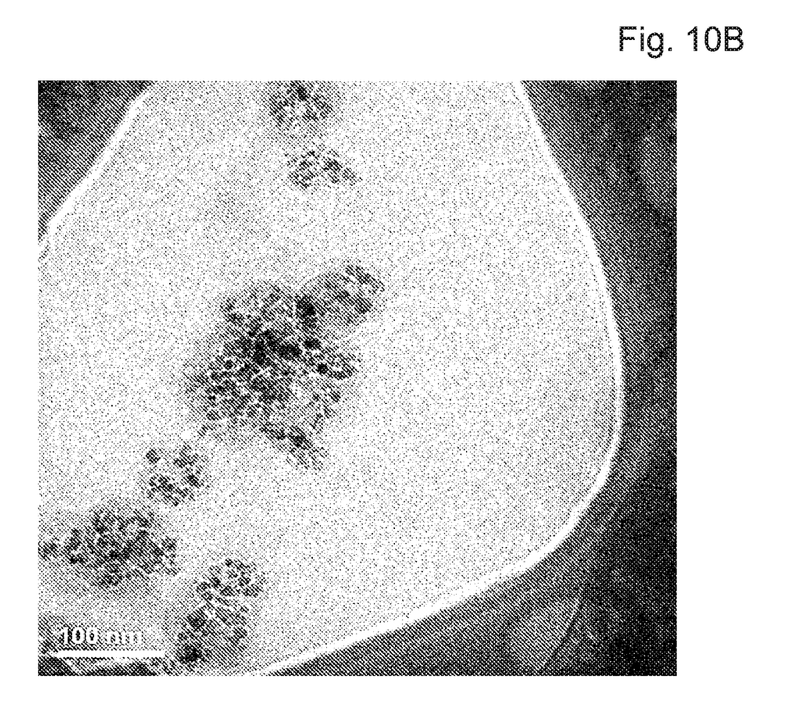
Figure 10C:
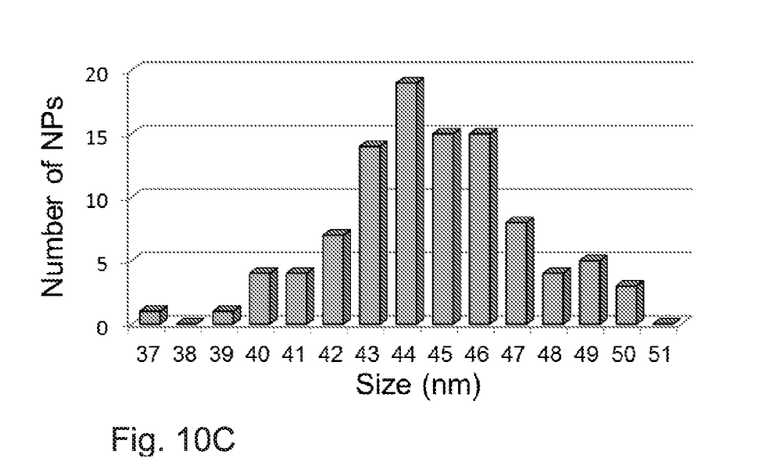
Figure 10D:
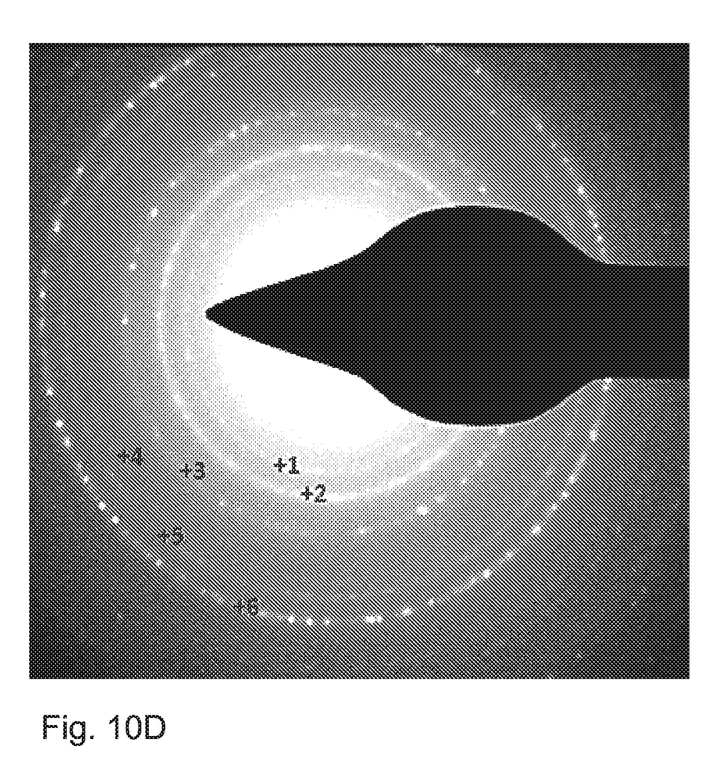
Figure 11A:
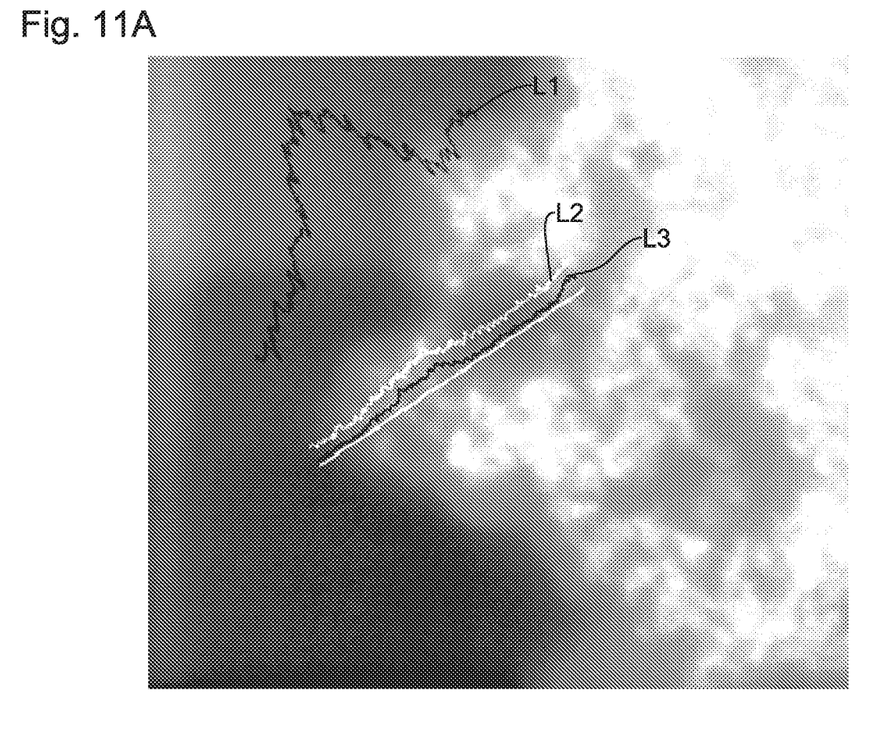
FIGS. 11A to 11D show measurement of amount of selected elements using HR-SEM image (FIG. 11A) and line scan analysis of HAS NPs for Carbon (FIG. 11B), Oxygen (FIG. 11C and Iron (FIG. 11D) according to some embodiments of the invention.
Figure 11B:
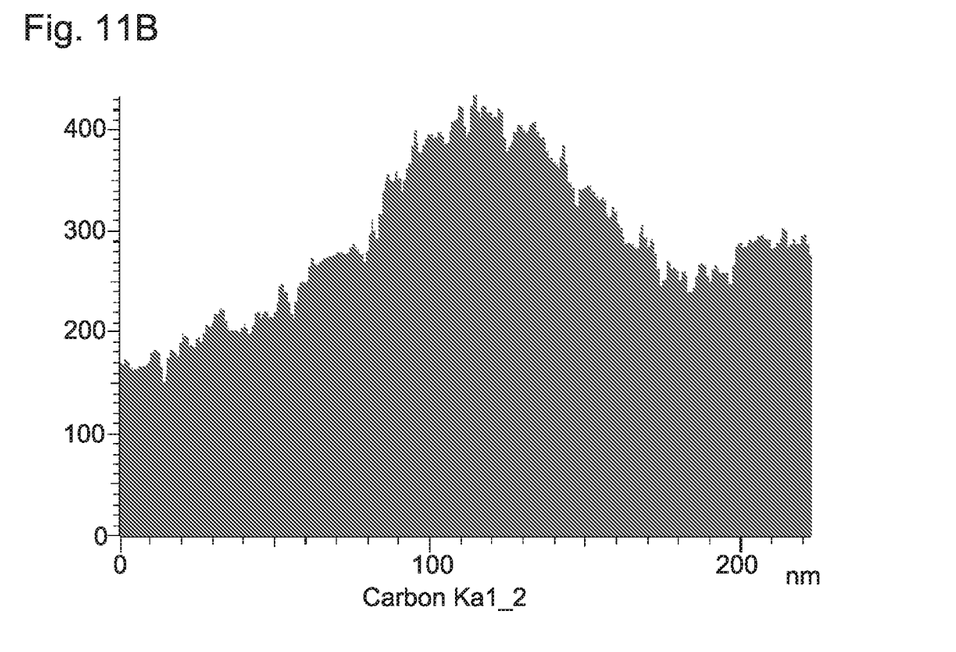
Figure 11C:
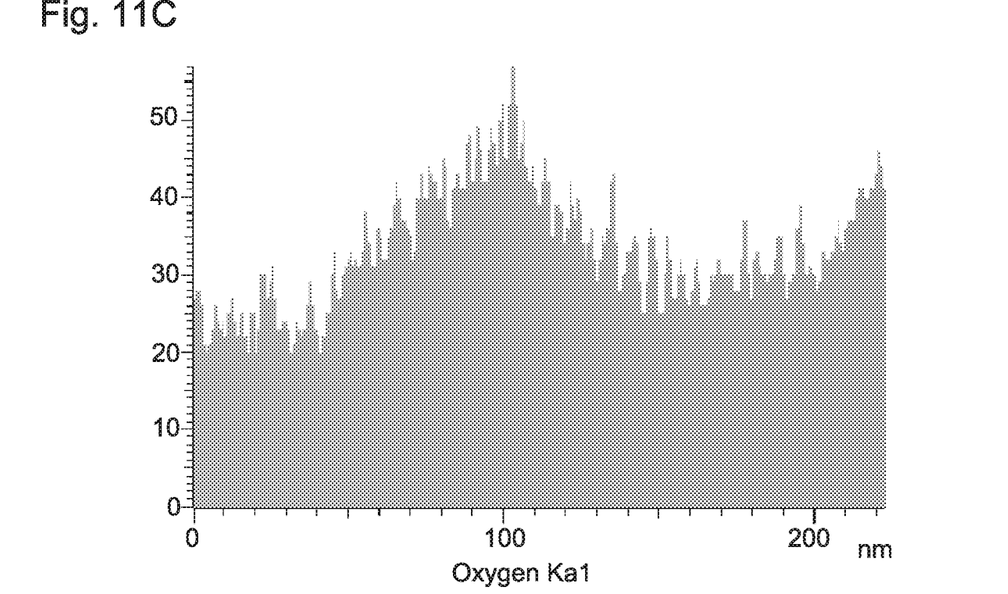
Figure 11D:
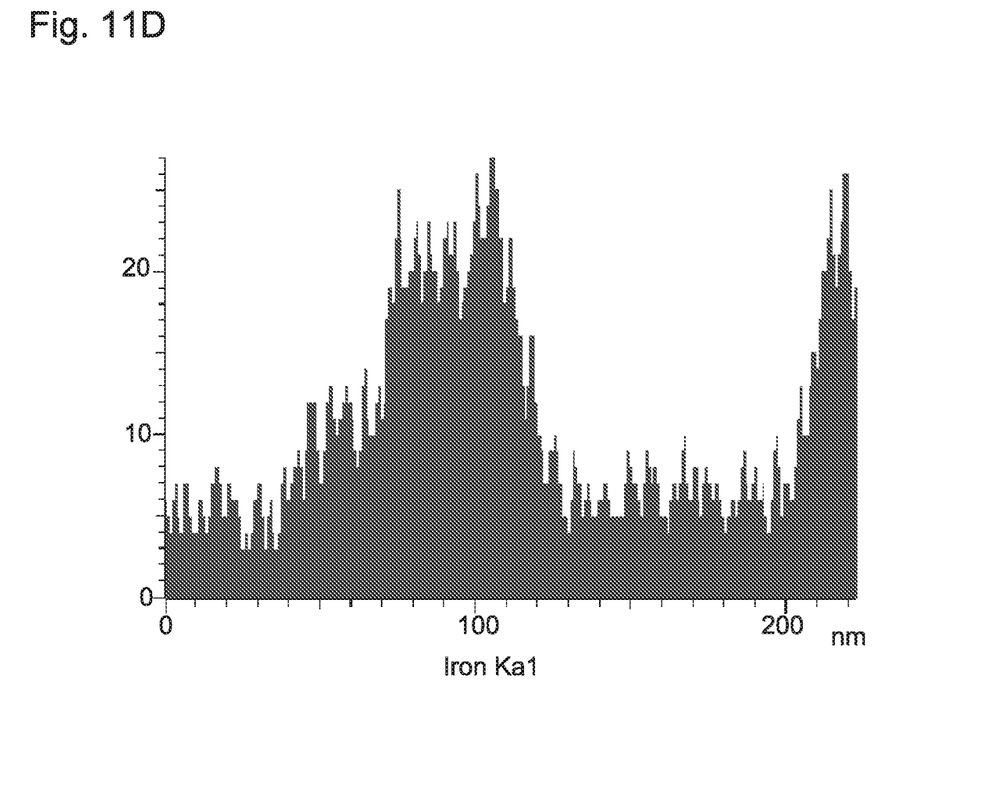

Reference is made to FIGS. 10A to 10D showing morphology and the size distribution measurements of the hybrid HSA/CAN-γ-$Fe_2O_3$ nanoparticles were characterized using TEM, cryo-TEM, and HR-SEM. FIGS. 10A and 10B show respectively TEM and cryo-TEM images of respectively the HSA NP phase (slightly less contrasting grey area) containing entrapped and strongly contrasting CAN maghemite NPs, which can be readily visualized and identified (dark spots) within the HSA phase. Hence, electron dense metallic NPs were successfully incorporated into the surrounding HSA matrix, while distributions of the CAN maghemite NPs between the particles and within each particle were found to be quite homogeneous, which likely arose from promoting interactions between the positively charged CAN-γ-$Fe_2O_3$ NPs and the negatively charged HSA phase. NP crystallinity has been further confirmed by TEM/Selected-Area Electron Diffraction (SA ED) as shows in FIG. 10D, in addition, the nanoparticles size distribution by TEM was also measured in FIG. 10C revealing an average size of 44.6±4.18 nm.

Figure 12:
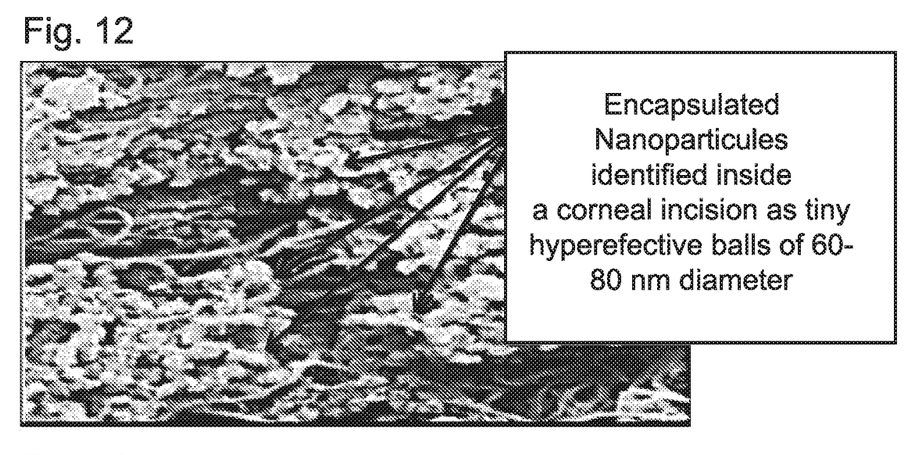
FIG. 12 shows reflection measurement from hyper reflecting iron particles embedded in the HAS NPs illustrating the NPs within the etched regions of the cornea.

FIGS. 11A to 11D show HR-SEM image (FIG. 11A) and line scan analysis for Carbon (FIG. 11B), Oxygen (FIG. 11C) and Iron (FIG. 11D) amounts obtained in a scanning transmission electron microscopy (STEM) mode. The can lines for analysis of the elements are marked as L1-L3 respectively for Carbon, Oxygen and Iron. The figure shows that CA maghemite NPs were present as fully encapsulated clusters in the HSA matrix, while the HSA phase appeared as surrounding clouds. The line-scan elemental analysis is based on Energy Dispersive X-ray Spectroscopy (EDS) validates that the CAN-γ-$Fe_2O_3$ NPs encapsulation mainly arose within the resulting HSA nanocomposite particles. Indeed, there is a simultaneous presence of iron (top-right), carbon (bottom-left), and oxygen (bottom-right) elements. The peak of the iron element is much thinner than the others, thus demonstrating the encapsulation of CAN-γ-$Fe_2O_3$ NPs into HSA NPs. Additionally, FIG. 12 shows reflection of iron particles embedded in the HAS NPs. As shown, from reflection of iron particles the HAS NPs are located within the incision region of the cornea enhancing the etched pattern.

ICP-AES elemental analyses were also carried out in order to confirm iron encapsulation during the hybrid NP formation. ICP measurements demonstrated an entrapment efficiency of 95% of elemental iron into the HSA phase. Additional concentration measurements of both the hybrid NPs and the CAN-maghemite NPs revealed that the weight percentage of the CA-maghemite NPs phase is nearly 40% out of the total weight of corresponding hybrid NPs.

Accordingly, the present technique utilizes solution formulation including albumin shell CAN-γ-$Fe_2O_3$ nanoparticles as eye drops enabling variation of refractive index at the selected etched patterns on the user cornea. The nanoparticles generally remain on the cornea for time period between a few days and a few months enabling correction of the user eye condition in accordance with optical operation of the selected pattern. The inventors have conducted tests on pig eyes validating optical effect of the etched pattern and selected nanoparticles for correction of optical vision impediment.

To this end, Refractive error of eight fresh pig eyes was measured with an automated refractometer before and after realization of a corneal superficial pattern and then after instillation of eye drops filled with the selected nanoparticles at a specific known concentration of between 0.1 mg/ml and 10 mg/ml. The nanoparticles' concentration used in this example was 1 mg/ml. In these tests, the pattern was applied to the cornea of the eye using a stamper, built by a 3-D printer with a calibrated optical pattern.

The stamper in this example is used to provide micro superficial erosion onto the cornea in order to let the nanoparticles penetrating the corneal epithelium, and thus enable desired optical power variation determined by the pattern. The pattern itself was selected to be a Fresnel plate zone diffractive pattern provide optical power of 2.5 diopters. Such additional optical power is generally suitable for vision assistance to user having Myopia. The optical power of the eye lenses was measured and recorded 5 times at each of the steps associated with the present technique. More specifically a baseline optical power was measured, optical power with patterned applied to the cornea, after application of the eye drop onto the eye at different time of immediately after drops instillation, 5 min, 10 min, 20 min and 30 min after instillation. The various measures were conducted to avoid bias due to large standard deviation.

Thus, after selection of the desired pattern in accordance with required optical correction, the two-dimensional pattern was applied to the cornea. When the pattern is etched on the cornea, the eye was washed with eye drop solution including HAS Maghemite nanoparticles. The nanoparticles were identified within the eye using iron marking of a portion of the nanoparticles. This enables identifying the nanoparticles using electron microscope (e.g. SEM) analysis.

Figure 13A:
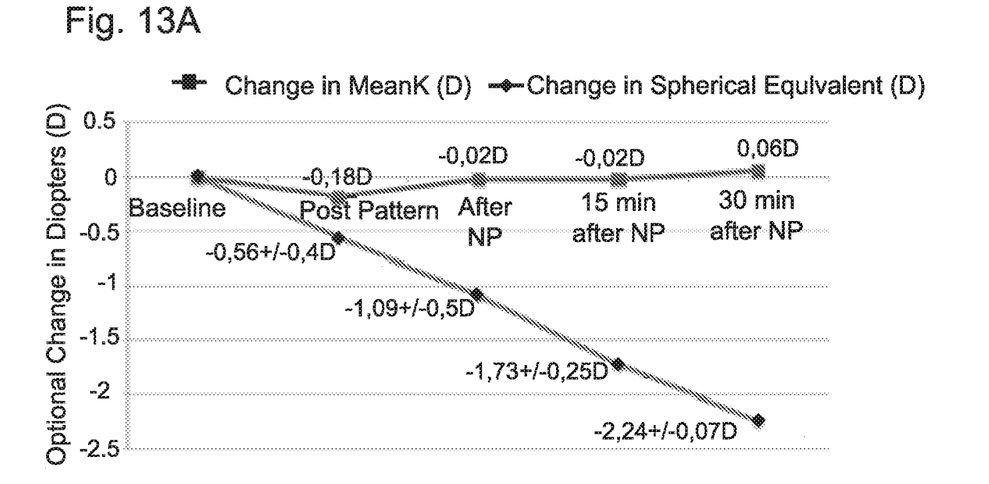
FIGS. 13A and 13B show measured variation in optical power of pigs' eyes provided by applying selected pattern on the eyes and providing eye drop solution according to some embodiments of the invention.
Figure 13B:
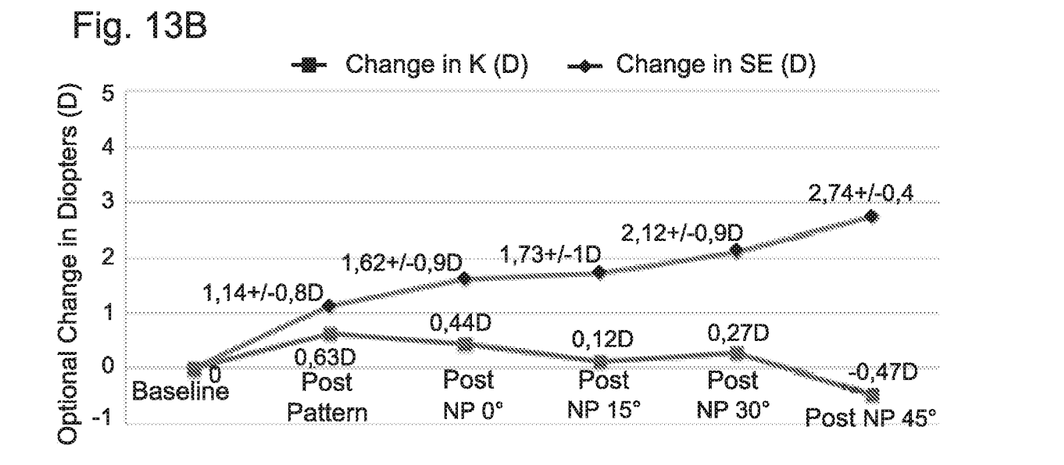

Reference is made to FIGS. 13A and 13B showing optical power variation results on pig eyes corrected using the above described technique. FIG. 13A show measurement results variation averaged over 4 pig eyes corrected by addition of 2.5 diopter optical power suitable for myopia correction. FIG. 13B shows similar results for addition of −2.5 diopter, generally suitable for presbyopia correction. FIGS. 13A and 13B also show measurement of corneal central keratometry indicative of variation of curvature of the central region of the cornea. As show, the applied pattern combined with the nanoparticles' eye drops provided mean correction of −2.24±0.07 diopter for myopic refractive error after 30 mn, and a correction of 2.74±0.2D for presbyopia correction after 45 mn on average. The corneal keratometry measurements show no statistically significant changes in the corneal central keratometry.

Accordingly, as shown, the use of selected pattern applied/etched on the cornea with suitable eye drops providing refractive index variation for reasonably long period enable correction of various eye conditions that requires no additional elements and is generally noninvasive. Generally, the pattern may be diffractive (e.g. Fresnel zone plate/rings) or configured to introduce light interference enabling extension of depth of focus of the eye.

Typically, the eye drops and corresponding nanoparticles as described here may be suitable for use in various additional conditions. For example, the eye drops solution described herein may be used for treatment of Dry eye disease (DED) where the nanoparticles provide lubrication to the eye operating as synthetic tears. DED represents a heterogeneous group of conditions with tear film insufficiency and signs and/or symptoms of ocular surface irritation. These conditions may be associated with various factors, including for example Meibomian gland dysfunction (MGD).

The use of the nanoparticles containing eye drops as described herein may be used for creating biological bond with the molecules of lipid composing the lipid layers of a user's eye. This results in both, greater stability of the tear film as well as longer effect onto the corneal surface.

Further, is should also be noted that the above described nanoparticles, being in eye drop solution may be used as drug delivery carriers. Generally, the anatomical barriers and physiological clearance mechanisms on the ocular surface presents challenges for development of ocular drug delivery devices. More invasive methods, such as intravitreal injections, can improve the ocular bioavailability of therapeutic agents but often result in vision-threatening side effects.

The use of the selected nanoparticles described herein may enhance the ocular bioavailability of one or more suitable therapeutic agents (e.g. drugs, proteins, peptides for example). The above described nanoparticles may provide major potential advantages, including for example improving of the penetration/bioavailability/delivery of any bioactive agent in deeper tissue for curing more severe affection such as bacterial, fungal or parasitic infection. Additional major advantage is associated with improving the bioavailability, which may lead to a significant decrease of eye-drops instillations frequency in chronic diseases such as glaucoma or dry eye diseases, as well as a potential external controllable drug delivery by portable device.

Thus, the present invention provides eye drop material composition carrying maghemite based nanoparticles with albumin shell. The eye drop composition may be used in combination with suitable patterning applied to cornea of a user's eye for providing selected optical correction to various eye conditions.

The invention claimed is:

1. A kit for use in correction of visual impediments, the kit comprising:
    a system for use in correction of eye condition, the system including a processing utility and an etching utility, wherein:
        the processing utility comprises a correction pattern module configured for providing a selected two-dimensional pattern in accordance with input data indicative of vision impediments of a user to provide selected optical correction effect of the user's eye, and for generating operational instructions to the etching utility for forming the selected two-dimensional pattern in the form of a surface relief in superficial layers of the cornea to provide said selected optical effect of temporary and targeted correction of refractive errors without modifying a corneal shape;
        the etching utility is configured to be responsive to the operational instructions to etch the selected two-dimensional pattern as the surface relief on a surface of the cornea of the user substantially without modifying a corneal shape; and
    eye drops including an aqueous solution having a plurality of nanoparticles made of biocompatible protein chains, said plurality of nanoparticles, being configured to be dispersed within incision regions of the surface relief of the cornea defined by said selected two-dimensional pattern on the surface of the cornea, thereby functionalizing and activating said optical correction effect and increasing stability of the optical correction effect of the selected two-dimensional pattern.

2. The kit of claim 1, further comprising an instruction manual for operating the system for etching the selected two-dimensional pattern in the superficial layers of the user's cornea without modifying the corneal shape, and applying the eye drops into the eye to disperse said nanoparticles in said incision regions of the surface relief.

3. The kit of claim 1 suitable for use at home or at a doctors' clinic.

4. The kit of claim 1, wherein the nanoparticles, when applied to the pattern on the surface of the cornea, enabling the optical correction effect lasting up to a few months.

5. The kit of claim 1, configured for performing at least one of the following: correction of at least one of myopia, hyperopia, presbyopia, astigmatism.

6. The kit of claim 1, wherein said selected two-dimensional pattern is configured to provide said optical correction effect comprising at least one of an optical power addition and increase of depth of focus.

7. The kit of claim 1, wherein said plurality of nanoparticles includes maghemite nanoparticles wrapped by biocompatible protein chains.

8. The kit of claim 1, wherein the biocompatible protein chains include human serum albumin proteins.

9. The kit of claim 1, wherein the plurality of nanoparticles are configured as a drug carrier.

10. The kit of claim 1, wherein the aqueous solution includes at least one of water, bacteriostatic water, sodium chloride solutions, glucose solutions, liquid surfactant, or pH-buffered solution.

11. The kit of claim 1, wherein said nanoparticles have refractive index different from at least one of a refractive index of the cornea and refractive index of tears around the eye.

12. The kit of claim 1, wherein the etching utility is configured for transmitting selected ultra-sound waves for etching said selected two-dimensional pattern on the surface of the cornea.

13. The kit of claim 1, wherein the etching utility is configured for mechanical etching of said selected two-dimensional pattern on the surface of the cornea.

14. The kit of claim 1, wherein the etching utility is configured for providing optical energy for etching said selected two-dimensional pattern on the surface of the cornea.

15. The kit of claim 1, wherein said selected two-dimensional pattern to be etched comprises at least one of a diffractive pattern and/or a phase effecting interference pattern.

16. The kit of claim 14, wherein the optical energy provides said etching at depth of up to a single cell layer of the cornea.

17. The kit of claim 14, wherein the etching utility comprises at least one laser unit and beam steering module and is configured for providing optical energy for creating the selected two-dimensional pattern in accordance with operation instructions on cornea of user's eye.

18. Kit of claim 1, wherein said two-dimensional pattern is configured to provide optical correction by optical power addition between 1 to 3 diopters.

19. The kit of claim 1, wherein said nanoparticles are further configured for carrying one or more selected drugs.

* * * * *